(12) United States Patent
Park

(10) Patent No.: US 8,238,998 B2
(45) Date of Patent: Aug. 7, 2012

(54) TAB ELECTRODE

(75) Inventor: Ik Ro Park, Wonju Si (KR)

(73) Assignee: Bio Protech Inc. (KR)

( * ) Notice: Subject to any disclaimer, the term of this patent is extended or adjusted under 35 U.S.C. 154(b) by 318 days.

(21) Appl. No.: 12/535,853

(22) Filed: Aug. 5, 2009

(65) Prior Publication Data
US 2010/0056896 A1 Mar. 4, 2010

(30) Foreign Application Priority Data
Aug. 27, 2008 (KR) .................. 10-2008-0084031

(51) Int. Cl.
*A61B 5/04* (2006.01)
(52) U.S. Cl. .................. 600/392; 600/391; 607/152
(58) Field of Classification Search .................. 600/391, 600/392; 607/149, 152, 153
See application file for complete search history.

(56) References Cited

U.S. PATENT DOCUMENTS

| | | | | |
|---|---|---|---|---|
| 4,353,372 A | * | 10/1982 | Ayer | 600/393 |
| 4,458,696 A | * | 7/1984 | Larimore | 607/152 |
| 4,653,501 A | * | 3/1987 | Cartmell et al. | 600/392 |
| 4,715,382 A | * | 12/1987 | Strand | 600/392 |
| 4,827,939 A | * | 5/1989 | Cartmell et al. | 600/392 |
| 6,076,002 A | * | 6/2000 | Cartmell et al. | 600/372 |

FOREIGN PATENT DOCUMENTS

| | | |
|---|---|---|
| KR | 1987-0006425 | 5/1987 |
| KR | 1989-0018028 | 12/1987 |
| KR | 1990-0006903 | 8/1990 |

* cited by examiner

*Primary Examiner* — Lee Cohen
(74) *Attorney, Agent, or Firm* — Gerald E. Hespos; Michael J. Porco

(57) ABSTRACT

A disposable tab electrode has core elements that include an adhesive conductive laminate layer and a logo sticker layer with a penetrating hole for contacting a sensor electrode. A protecting film is put around both ends of the core elements. As a result, the disposable tab electrode can be made inexpensively, stored hygienically for a long time and used easily. A lead wire for connecting to the tab electrode has a projection on one end of a sensor electrode that is adhered onto the conductive laminate layer of the disposable tab electrode. The projection is fixed to the lead wire body by a fixing member. As a result, expensive Ag—AgCl electrode sensors can be used repeatedly. The lead wire can have a nipper self-contained or integrated with the lead wire body to prevent the lead wire from separating from the disposable tab electrode during use.

3 Claims, 5 Drawing Sheets

TAB ELECTRODE

BACKGROUND OF THE INVENTION

1. Field of the Invention

The present invention relates to a tab electrode, and more particularly to a disposable tab electrode for sensing bioelectrical signals of living body such as a human body and a lead wire which can be joined into the disposable tab electrode repeatedly.

2. Description of the Related Art

An electrode for living body is adhered closely to a surface of outer layer of skin of living body, and it is for sensing bioelectrical signals exposed by the activities of heart, brain, muscle and so on. It is an essential part for electrocardiographs.

In a conventional electrode for living body 1, as shown in FIGS. 1 and 2 (refer to Korean Utility model Publication No. 20-1990-0006903), a disclosed part 3 is formed in the inner side of a skin adhering part 2 and 2a, a lead wire connecting apparatus 4 and a disc type electrode part are formed in the disclosed part, and a lead wire connecting part 4a is formed on the lead wire connecting apparatus 4.

A lead wire 6 connecting to a conventional electrode for living body, as shown in FIG. 3 (refer to Korean Utility model Publication No. 20-1990-0006903), is joined by a lead wire connecting body 7 having a concave part 7a to surround the lead wire connecting part 4a. In FIG. 3, reference number 8 is a water-containing gel for reducing contact resistance of living body.

As described before, a disc-type electrode part 5, which is made of expensive Ag—AgCl, and a lead wire connecting apparatus 4 are essentially formed in the conventional electrode for living body 1, and therefore, the conventional electrode should be bulky and expensive, and every time measuring minute voltage, there has been inconvenience that the gel containing water 8 should be attached to under the disc-type electrode 5.

Because a lead wire 6 connecting to a conventional electrode is connected to the lead wire connecting part 4a by simple insertion by a lead wire connecting body 7 having a concave part 7a, problems such as inferiority of electrical contact and easy breakaway of the lead wire from an electrode by minor movement often arise with the conventional lead wire.

SUMMARY OF THE INVENTION

To solve the problems which the conventional tab electrode and lead wire have, the present invention is directed to a disposable tab electrode which can be produced in large quantities with cheap price and a lead wire which can be joined and applied to the disposable tab electrode repeatedly.

To achieve the objective of the present invention, a disposable tab electrode is characterized by comprising a rectangular or circular bottom film; an adhesive conductive laminate layer adhered onto the bottom film with smaller size than the bottom film; a logo sticker layer having a penetrating hole in the middle of it, adhered onto the conductive laminate layer with the same or larger than the conductive laminate layer in size; and a cover film adhered onto the disclosed conductive laminate layer through the penetrating hole of the logo sticker layer.

A lead wire for connecting to a tab electrode is characterized by a sensor electrode that one end of the sensor electrode is adhered onto the part of the conductive laminate layer disclosed through the penetrating hole of the logo sticker layer and the other end of the sensor electrode has a projection; a lead wire body which the projection of the sensor electrode is inserted into and electrically connected to; and one or more sensor electrode fixing members which can fix the projection of the sensor electrode to the lead wire body or release it.

The present invention embodies a disposable tab electrode by removing the conventional sensor electrode and the lead wire connecting part, making an adhesive conductive laminate layer and a logo sticker layer having a penetrating hole for making contact with a sensor electrode as core elements, and putting protecting films around both ends of the core elements. As a result, it is possible to produce the disposable tab electrode in large quantities with cheap price. When using a disposable tab electrode of the present invention, user may cut a disposable tab electrode as much as need be or in stamped size and remove the protecting film around both ends only. Therefore, it is possible to keep hygienic storage of the disposable tab electrode for a long time and make use of it easily.

And the present invention embodies a lead wire for connecting to the tab electrode by forming a projection on one end of a sensor electrode which is adhered onto the conductive laminate layer of the disposable tab electrode, and fixing the projection to the lead wire body by a fixing member. As a result, it is possible to use expensive Ag—AgCl electrode sensor repeatedly. The lead wire of the present invention can further comprise a nipper self-contained or integrated with the lead wire body. It can prevent the lead wire separating from the disposable tab electrode when it is being used.

Reference number 10 is a lead wire body, 20 means a sensor electrode, 30 is a cable, 40 means a nipper, 50 indicates a lead wire body integrated with a nipper, 100 is a patch comprised of a plurality of disposable tab electrodes, 110 is a bottom film, 120 means a conductive laminate layer, 130 indicates a logo sticker layer, and 140 is a cover film.

DETAILED DESCRIPTION OF THE PREFERRED EMBODIMENTS

A detailed description of preferred embodiments of the present invention is provided below with respect to the accompanying drawings.

Figure 5:
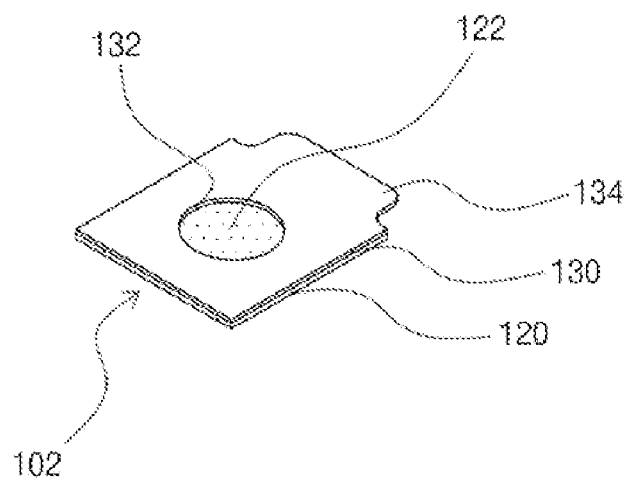
FIG. 5 is a skew drawing showing a kernel structure of a disposable tab electrode according to the present invention.

First, a disposable tab electrode, as shown in FIG. 5, comprises basically an adhesive conductive laminate layer 120 and a logo sticker layer 130 having a penetrating hole 132 for making contact with a sensor electrode as core elements 102.

Figure 1:
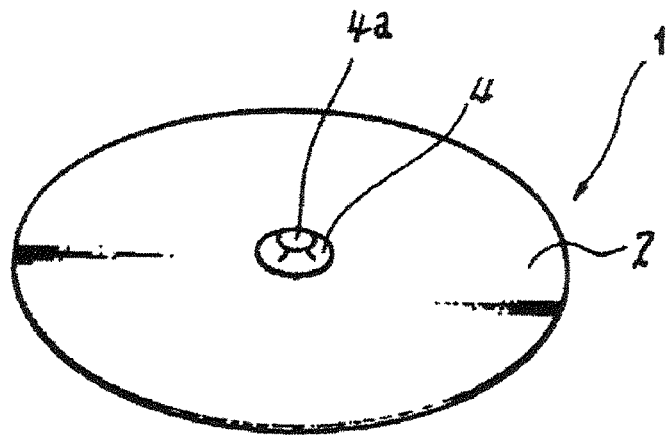
FIGS. 1 and 2 show structures of conventional electrodes for living body.
Figure 2:
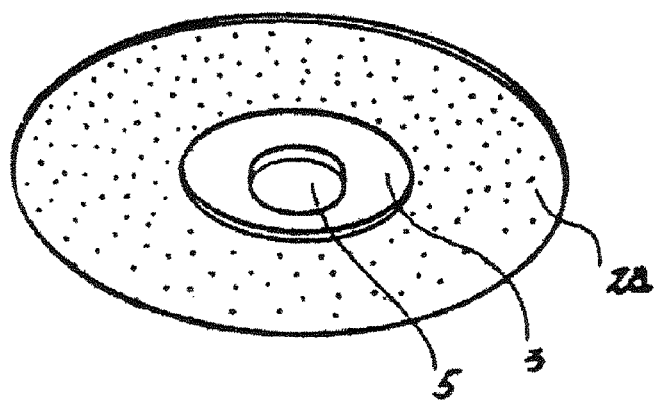
Figure 3:
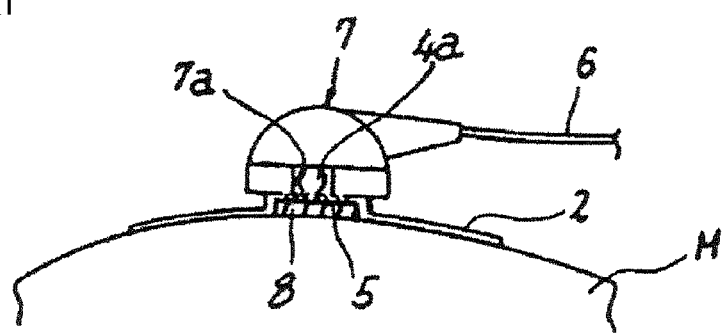
FIG. 3 shows a structure of a lead wire connecting to a conventional electrode for living body.
Figure 4:
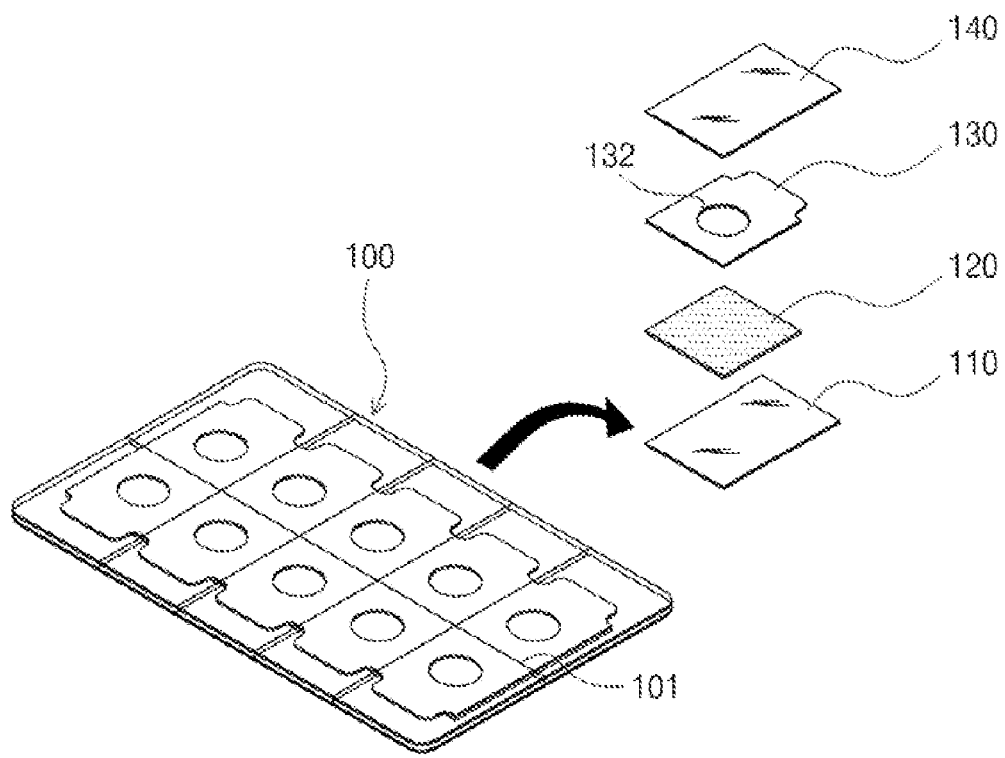
FIG. 4 is a skew drawing illustrating a patch comprised of a plurality of disposable tab electrodes and a single disposable tab electrode according to the present invention.

And the disposable tab electrode, as shown in FIG. 4, further comprises protecting films 110 and 140 putting around both sides of the core elements in order to produce in large quantities and keep a hygienic storage for a long time.

Therefore, when user cut a disposable tab electrode patch 100 following to the stamped line 101, the disposable tab electrode comprises a rectangular bottom film 110; an adhesive conductive laminate layer 120 adhered onto the bottom film with smaller size than the bottom film; a logo sticker layer 130 having a penetrating hole 132 in the middle of it, adhered onto the conductive laminate layer with the same or larger than the conductive laminate layer in size; and a cover film 140 adhered onto a part 122 of the conductive laminate layer 120 disclosed through the penetrating hole 132 of the logo sticker layer as its basic components.

Here, the shape of the bottom film 110 can be circular, and the size of the cover film 140 to cover the disclosed conductive laminate layer 120 through the penetrating hole 132 is big enough, but, as shown in FIG. 4, it is preferable that the size of the cover film 140 is about the same as that of the bottom film 110 from a point of view about mass production. And it is preferable that the size of the logo sticker layer 130 is the same as that of the conductive laminate layer 120 from a point of view about mass production.

Figure 10:
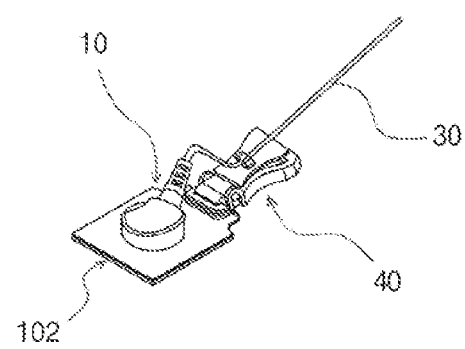

The logo sticker layer 130 includes one or more things selected from printing papers, nonwoven fabric, PE(polyethylene) foam and PET(polyethylene terephthalate) film on which a logo such as a product name is to be printed. As shown in FIG. 4, it is preferable that the size is smaller than that of a bottom film 110 and larger than that of a conductive laminate layer 120 to remove both films 110 and 140 at both ends easily. It is preferable that the logo sticker layer has one side end part 134 which does not attach to the conductive laminate layer 120 in order that the one side end part 134 functions as a grasp for a tab electrode, and as space for fixing a lead wire by a nipple 40 of a lead wire for connecting to a tab electrode, as shown in FIG. 10.

It is preferable that the conductive laminate layer 120 is hydro-gel which has adhesive property to the surface of living body like human body and is excellent in conductivity. However, any material which has adhesive property to skin and is able to reduce contact resistance with a sensor electrode can be used for the conductive laminate layer.

It is sufficient that the bottom film 110 and the cover film 140 are a transparent and thin vinyl film. However, it is more preferable for the bottom film and the cover film to be made of PE(polyethylene) or PET(polyethylene terephthalate).

The penetrating hole 132 formed at the logo sticker layer 130 is intended to reveal a lower conductive laminate layer 120, and to attach a sensor electrode plate of a lead wire onto it for connecting to a tab electrode. Therefore, the penetrating hole should be formed considering the size and shape of a sensor electrode plate.

Next, a detailed description of another embodiment of a lead wire for connecting to the disposable tab electrode of the present invention is provided below.

Figure 6:
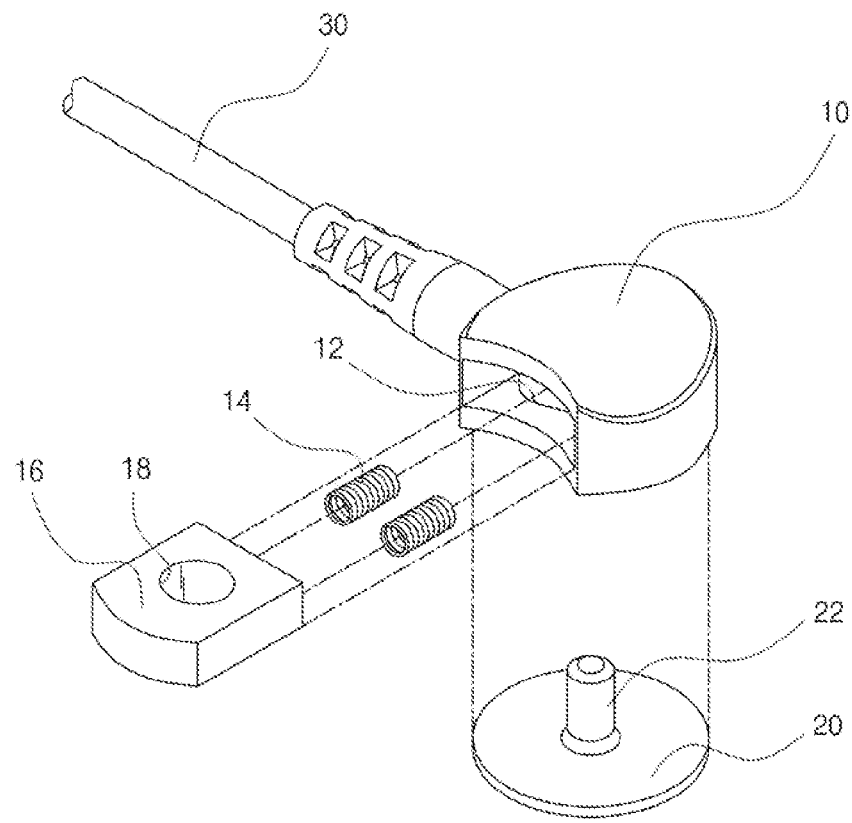
FIG. 6 is an exploded skew drawing showing a connecting relationship of elements of a lead wire for connecting to a tab electrode according to the present invention.
Figure 8:
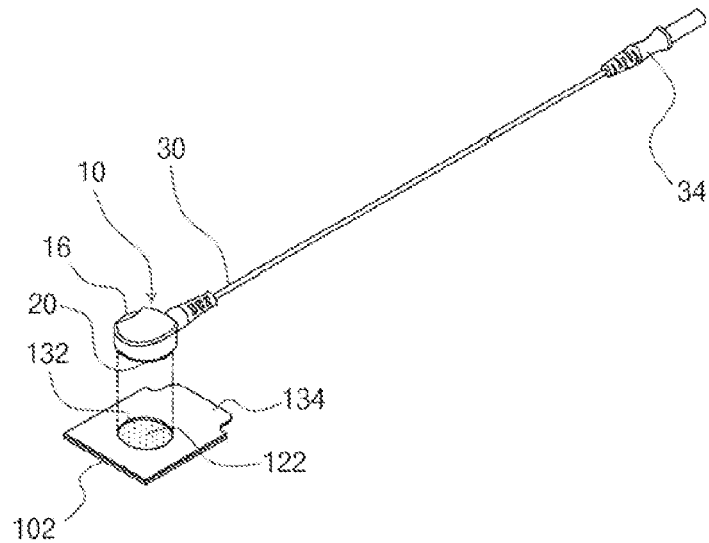
FIGS. 8 to 12 show states of connecting a lead wire to a disposable tab electrode according to the present invention.

A lead wire for connecting to the tab electrode of the present invention, as shown in FIGS. 6 and 8, basically, comprises a sensor electrode 20 that one end of the sensor electrode is adhered onto the part 122 of the conductive laminate layer 120 disclosed through the penetrating hole 132 of the logo sticker layer 130 and the other end of the sensor electrode has a projection 22; a lead wire body 10 which the projection 22 of the sensor electrode 20 is inserted into and electrically connected to; and one or more sensor electrode fixing members 14, 16, etc., which can fix the projection 22 of the sensor electrode 20 to the lead wire body 10 or release it.

Figure 7:
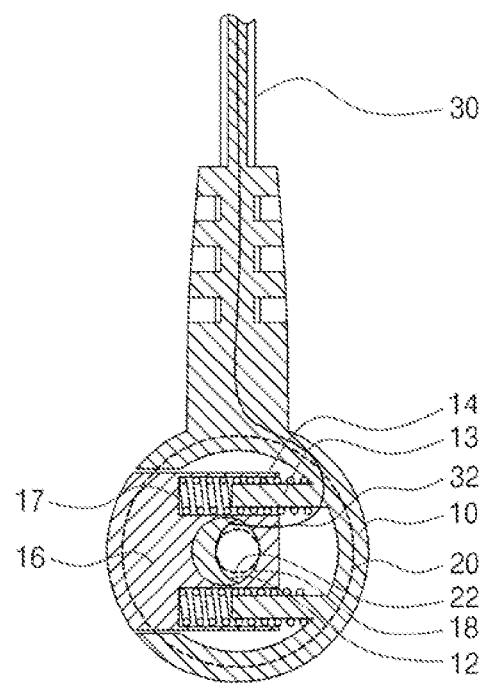
FIG. 7 is a cross sectional view when a sensor electrode is connected to a lead wire for connecting to a tab electrode according to the present invention.

More specifically, as shown in FIGS. 6 and 7, the lead wire body 10 has one side disclosed for the sensor electrode fixing members 14, 16, etc. to be equipped, two pillars 13 formed separately toward the disclosed side at the inner side, and an insertion hole 12 formed perpendicularly with the each pillar on at least under part of the lead wire body 10 for the projection 22 of the sensor electrode 20 to be inserted into and contacted with it, coated with conductive material to the inner side of it, and the sensor electrode fixing members are comprised of two springs 14 inserted onto the two pillars 13 respectively; and a mobile fixing key 16 having two long grooves 17 formed at both sides for holding each of the springs inserted onto the pillars and a hole 18 formed at the middle for the projection 22 of the sensor electrode 20 to penetrate.

With the above-mentioned formation, as shown in FIG. 6, when two springs 14 are respectively inserted onto two pillars 13 projected toward the inner side of the lead wire body 10, and a mobile fixing key 16 is put into the lead wire body 10 of which one end is disclosed so as that the other end of each spring 14 is made fit to a long groove 17, and the projection 22 of the sensor electrode 20 is made fit to the insertion hole 12 and the hole 18 of the mobile fixing key 16, as shown in FIG. 7 of a cross sectional view, by elasticity of two springs 14, the projection 22 of the sensor electrode 20 is contacted closely to the inner side of the insertion hole 12 onto which conductive material is applied, and is fixed at between the insertion hole 12 and a hole 18 of a mobile fixing key 16.

In reverse, in order to separate the sensor electrode 20 from the lead wire body 10, user can pull the sensor electrode 20 out with pressing the mobile fixing key 16. So, it is easy to replace a sensor electrode.

In order to adhere the lead wire for connecting to a tab electrode to a disposable tab electrode, as shown in FIG. 8, user can attach the lead wire body 10, which the sensor electrode 20 is joined, to the insertion hole 132 of a disposable tab electrode 102 which has been already attached to a living body.

Then, the adhesive strength of the conductive laminate layer 120 of a disposable tab electrode 102 can make a sensor electrode 20, further a cable 30 attached. So, it is possible to conduct a simple examination with the above-mentioned formation only.

Figure 9:
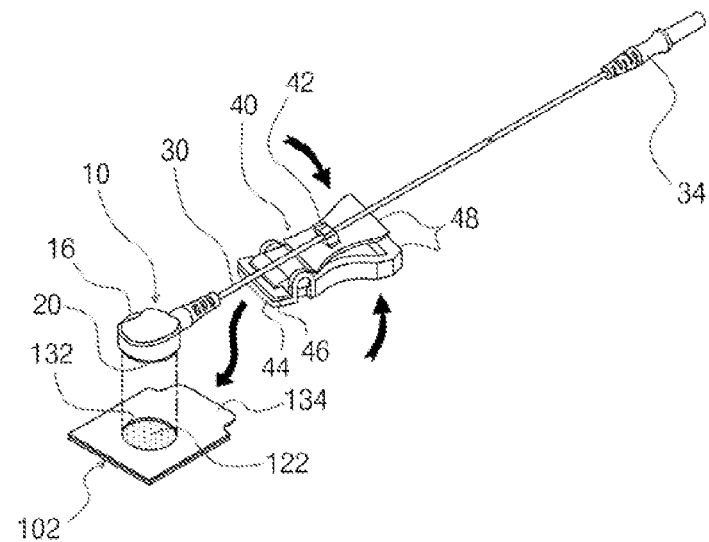

However, for a long-time examination or with examinee's movement, a lead wire 30 can be separated from a tab electrode 102. To prevent a cable 30 separating from a tab electrode 102, it is more preferable that a lead wire further comprises a nipper 40 for fixing the logo sticker layer 134, wherein the nipper 40 is attached to the cable 30 connected to one end of the lead wire body 10, as shown in FIGS. 9 and 10. Or, as shown in FIGS. 11 and 12, a lead wire body 50 integrated with a nipper for fixing the logo sticker layer 134 is more preferable.

Figure 11:
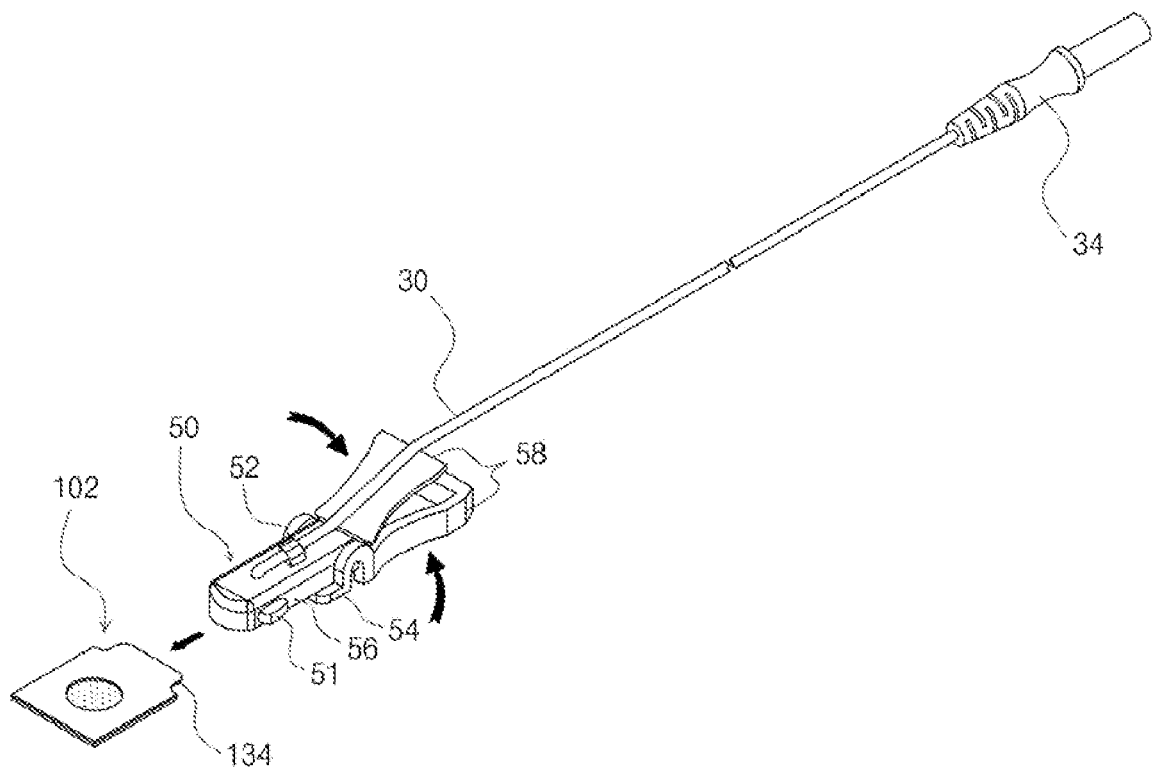
Figure 12:
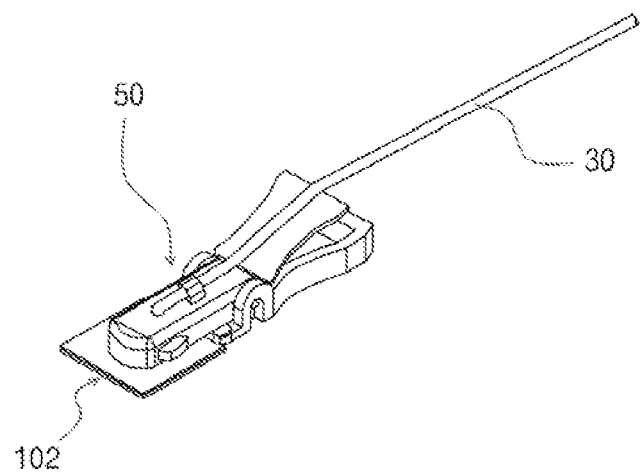

In FIGS. 9 and 11, reference number 42 and 52 are a fixing ring of a lead wire, 44 and 54 are a lower nipper jaw, 46 and 56 are a upper nipper jaw, 48 and 58 is a grip, and 34 is a lead wire plug.

In order to attach a lead wire for connecting to a tab electrode with a separate nipper to a disposable tab electrode, as shown in FIG. 9, user can put a lead wire body 10 to which the sensor electrode 20 is joined on the insertion hole 132 of a disposable tab electrode 102 which has been attached to the surface of living body, tighten a grip 48 of a nipper 40, widen the space between the lower and upper nipper jaws 44 and 46, and let a nipper hold one side end part 134 of the logo sticker layer 130 which is not attached to the conductive laminate layer 120 of a tab electrode, as shown in FIG. 10.

In order to attach a lead wire for connecting to a tab electrode with an integrated nipper to a disposable tab electrode, as shown in FIG. 11, user can tighten a grip 58 of a nipper integrated into the lead wire body 50, widen the space between the lower and upper nipper jaws 54 and 56, move the lead wire toward a disposable tab electrode 102 which has been attached to the surface of living body, place the lead wire body 50 onto the insertion hole 132 of a tab electrode 102, and hold one end part 134 of the logo sticker layer 130 which is not attached to the conductive laminate layer 120 of a tab electrode between the lower and upper nipper jaws 54 and 56. Then, as shown in FIG. 12, a sensor electrode can be joined together at the same time.

In FIG. 11, reference number 51 means a mobile fixing key which performs the same function as reference number 16 in FIGS. 9 and 7.

What is claimed is:

1. A disposable tab electrode comprising:
   a rectangular or circular bottom film;
   an adhesive conductive laminate layer adhered onto the bottom film, the adhesive conductive laminate layer being smaller than the bottom film and larger than a sensor electrode to be attached;
   a logo sticker layer adhered onto the conductive laminate layer, the logo sticker layer being larger than the conductive laminate layer and smaller than the bottom film, a penetrating hole formed through a middle portion of the logo sticker layer, the logo sticker layer further having one side end part that is not attached to the adhesive laminate layer to define a tab that can be gripped by nipping means for fixing a lead wire to the tab; and
   a cover film adhered onto a part of the conductive laminate layer disclosed through the penetrating hole of the logo sticker layer.

2. The disposable tab electrode of claim 1,
   wherein the conductive laminate layer is hydro-gel.

3. The disposable tab electrode of claim 2,
   wherein the bottom film and the cover film are polyethylene (PE) or polyethylene Terephthalate (PET),
   wherein the logo sticker includes one or more things selected from printing papers, nonwoven fabric, polyethylene (PE) foam and polyethylene terephthalate (PET) film,
   and wherein the penetrating hole of the logo sticker layer is in circular shape.

* * * * *